United States Patent [19]

Gillespie

[11] 3,930,991

[45] Jan. 6, 1976

[54] MEAT PROCESSING

[75] Inventor: Robert M. Gillespie, Grand Rapids, Mich.

[73] Assignee: Sortex Company of North America, Inc., Lowell, Mich.

[22] Filed: Oct. 25, 1974

[21] Appl. No.: 517,969

Related U.S. Application Data

[62] Division of Ser. No. 297,347, Oct. 13, 1974, Pat. No. 3,851,074.

[52] U.S. Cl. ............................. 209/3; 209/111.6
[51] Int. Cl.² ............................. B07C 5/342
[58] Field of Search .......... 209/3, 111.6, 11, 111.5, 209/111.7; 99/489; 356/157; 250/223 R

[56] References Cited
UNITED STATES PATENTS

| | | | |
|---|---|---|---|
| 2,020,843 | 11/1935 | Lohner | 426/513 |
| 2,373,361 | 4/1945 | Walter | 99/489 |
| 2,531,343 | 11/1950 | Patterson | 209/3 |
| 3,011,634 | 12/1961 | Hutter et al. | 209/111.7 UX |
| 3,499,527 | 3/1970 | Badgley | 356/157 X |
| 3,545,610 | 12/1970 | Kelly et al. | 209/111.7 X |
| 3,650,396 | 3/1972 | Gillespie et al. | 209/3 |

*Primary Examiner*—Frank W. Lutter
*Assistant Examiner*—Ralph J. Hill
*Attorney, Agent, or Firm*—McGarry & Waters

[57] ABSTRACT

A meat processing system and method wherein trim pieces of meat having lean meat portions and fat meat portions are divided into smaller regular sized meat chunks of higher lean meat content and chunks of higher fat content. The chunks are passed seriatim through a photometric sensing zone to photometrically detect an optical property related to the lean meat or fat content of the meat chunks and the meat chunks are thereafter sorted in accordance with the value of the optical property sensed in the photometric sensing zone. Meat chunks of higher lean meat content are thereby sorted from chunks of higher fat content. The temperature of the meat chunks is maintained at or near the freezing temperature to facilitate singularizing and handling of the meat chunks so that the meat chunks can be passed seriatim through the photometric sensing zone.

9 Claims, 4 Drawing Figures

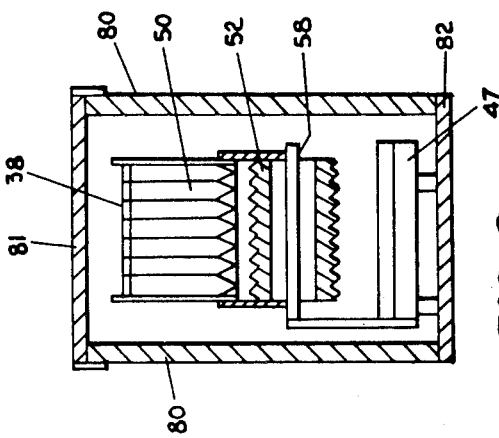
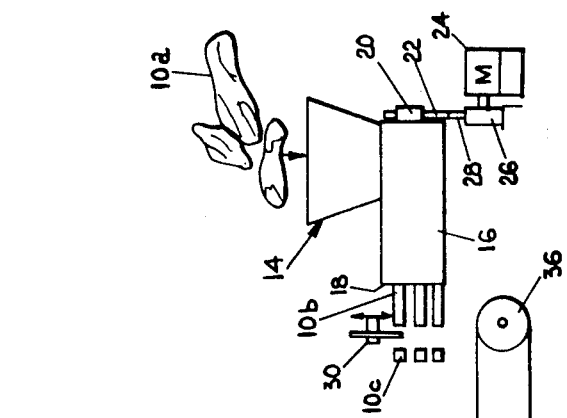
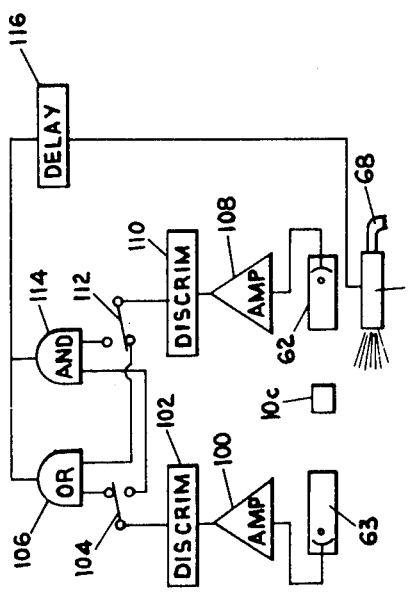
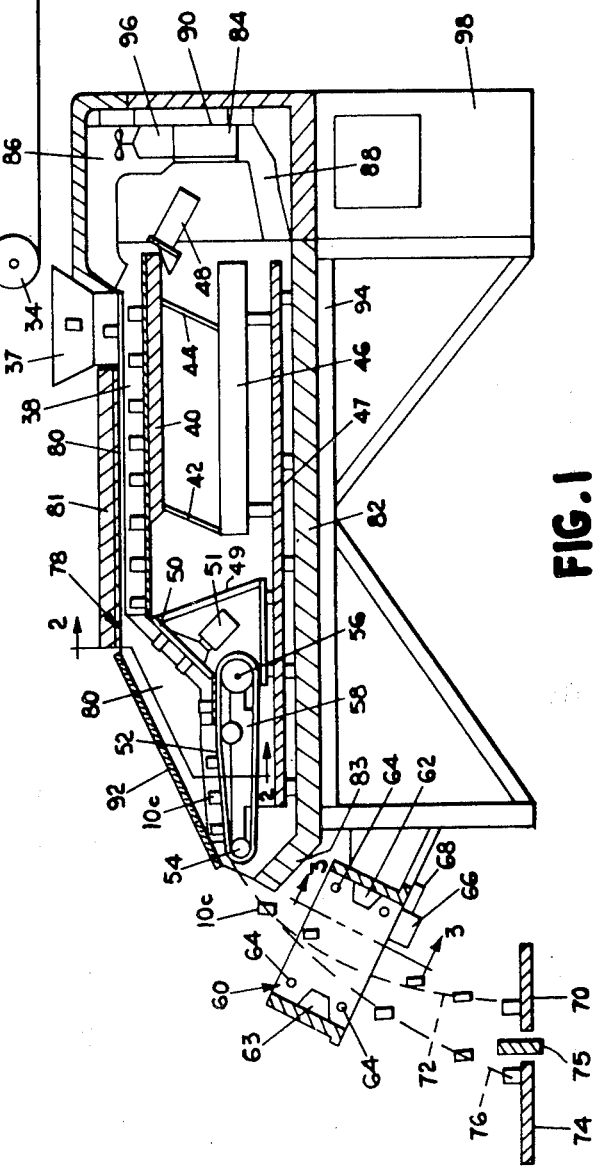

MEAT PROCESSING

This application is a division of U.S. patent application Ser. No. 297,347, filed Oct. 13, 1974, now U.S. Pat. No. 3,851,074.

BACKGROUND OF THE INVENTION

1. Field of the Invention

This invention relates to processing trim meat pieces. In one of its aspects, the invention relates to upgrading trim pieces of meat to a fraction having a higher lean meat content and a fraction having a higher fat content.

2. State of Prior Art

Knudsen, U.S. Pat. No. 3,396,280, discloses a method for determining the fat content of trimmings or similar pieces of meat by photoelectrically sensing the color of each such meat piece and integrating the value thus photoelectrically sensed to give a percentage of fat content in a batch of meat. The batch can then be upgraded by adding lean pieces of meat if the lean meat content is too low.

Badgley, U.S. Pat. No. 3,499,527, discloses a method and apparatus for selectively separating meat products such as strips of bacon by projecting a green light on the surface areas of the meat products and detecting the intensity of the green light reflected therefrom. Typically, a batch of meat products, such as bacon strips, will be photoelectrically measured at a particular time to make certain that the meat products have a predetermined ratio of lean to fat meat. In the event that the products have a content of meat which is too low, a warning light is turned on and the meat products are removed selectively from a conveyor system.

Kail, in U.S. Pat. No. 3,154,625, discloses a photometric method for grading beef wherein a portion of a ribeye meat cut of beef is photoelectrically viewed with and without a filter, and the light value detected is correlated with the weight of the animal to give a meat yield and a quality grade for the animal.

Walter, in U.S. Pat. No. 2,373,361 discloses an apparatus for separating lean meat from fat tissue wherein fat trimmings are ground up and deposited on a belt. The ground meat is pressed into a thin layer on the belt and then cut into thin ribbons of about ½ inch to 1 inch in thickness. Light reflected from the ribbons is sensed by a photoelectric cell. Scrapers are operated in accordance with the light detected from the photoelectric cell to scrape lean meat from the belt into a first chute. The fatter portions remain on the belt and are later scraped therefrom into a second chute. The process depends on the grinding of the meat into coarse particles so that it can be flattened onto a belt and also depends on the stickiness of the meat to adhere to the belt.

SUMMARY OF THE INVENTION

A method and system has now been discovered for upgrading a particular quantity of trim meat pieces which may be cut from selected meat portions or may comprise fatter portions of animals. The trim pieces are upgraded to give a saleable meat product by dividing the trim meat into a plurality of substantially regular size chunks, passing the meat chunks seriatim through a photometric sensing zone and therein photometrically detecting an optical property related to the quantity of lean meat or fat within the meat chunks, and thereafter sorting the meat chunks in accordance with the value of the optical property thus detected to sort the meat into a fraction having a higher lean meat content and a fraction having a lower lean meat content. The dividing step, which preferably comprises extruding the trim meat pieces through a die opening and cutting the extruded meat portions into chunks, tends to separate the meat into chunks of higher lean meat content and chunks of lower lean meat content. Desirably, the meat chunks are of a substantially regular size, either cylindrical or cubical in shape and have a mean average diameter in the range of ¼ to 1 inch, and preferably of approximately ½ inch mean average diameter.

In accordance with one embodiment of the invention, the meat chunks are passed in a free-fall trajectory through the photometric sensing zone and those meat chunks having a given optical value are deflected after they are sensed in the photometric detecting zone. The optical property of the meat chunk detected is preferably the color so that the light value photometrically sensed is proportional to the fat content of the meat chunks. If necessary, a filter can be used to accentuate the difference between lean meat and fat.

Desirably, the temperature of the meat chunks is maintained at a low temperature, desirably about the freezing point, to assist in singularizing the meat chunks for feeding to the photometric detecting zone.

Also, according to the invention there is provided a system for processing trim meat pieces having lean portions and fat portions. The apparatus includes a means for dividing the trim meat pieces into substantially regular shape meat chunks having a high lean meat content and having a high fat content, means for singularizing the meat chunks and a photometric sensing means positioned to view individually the singularized meat chunks for detecting an optical property of each of the meat chunks. Means are further provided to sort the meat chunks according to the value of the optical property thus sensed so that the meat chunks are sorted to achieve a fat rich concentrate and a lean meat concentrate.

In a preferred embodiment of the invention, the sensing means includes means to detect the optical property at opposite sides of the meat chunks. An OR gate circuit is provided to separate the meat chunks when the optical property of either side of the meat chunks exceeds a predetermined value. In addition, an AND gate circuit is provided to separate the meat chunks only when the optical property of both sides thereof exceeds a predetermined value. A switch is provided for selection of the AND gate or the OR gate mode of operation.

BRIEF DESCRIPTION OF THE DRAWINGS

The invention will now be described with reference to the accompanying drawings in which:

FIG. 1 is a schematic representation of a side elevational view, partly in section, of a meat processing system according to the invention;

FIG. 2 is a partial sectional view taken along lines 2—2 of FIG. 1;

FIG. 3 is a partial sectional view taken along lines 3—3 of FIG. 1; and

FIG. 4 is a schematic representation of an electrical control system for operation of an ejector.

DESCRIPTION OF THE PREFERRED EMBODIMENT

Referring now to the drawings, a hopper 14 receives trim meat 10a which typically has been trimmed from portions of an animal having a relatively high meat content. The trim meat 10a has portions thereof with lean meat, although predominantly will be of a high fat content. The trim meat 10a fed to the hopper 14 passes into an extruder 16 containing a suitable auger (not shown) driven by a drive shaft 20. A motor 24 drives the shaft 20 conventionally through a pulley 26, a belt 28, and a pulley wheel 22 on the drive shaft 20.

In the extruder 16, the trim meat 10a is divided into smaller pieces and extruded through the die plate 18. The extruded meat 10b is cut into regular size meat chunks 10c by a suitable cutting means 30 as, for example, a rotating knife blade which reciprocates vertically to shear the meat into chunks 10c. The separation and cutting process tends to liberate the fat from the meat, yielding meat chunks having a high percentage of lean meat and chunks having a high percentage of fat. Desirably, the meat chunks are cut into cylindrical pieces of approximately ½ inch in length by ½ inch in diameter. The size of the meat chunks can vary. Generally, the mean diameter of the meat chunks will range from ¼ inch to 1 inch and the mean length of the cylinders can range from ¼ inch to 1 inch. The meat chunks are desirably substantially cubical or cylindrical in shape with the size and diameter of the chunks being about equal. However, any regular shape chunks would be suitable so long as the mean average diameter is in the range of about ¼ inch to 1 inch.

The meat chunks 10c are fed by a conveyor 32 to a hopper 37 and onto a vibratory feeder tray 38. The conveyor belt 32 is trained conventionally around pulley wheels 34 and 36. The vibratory feeder tray is secured to a support 40 which has a pair of resilient mounting plates 42, 44 and a base member 46. A vibratory motor 48 drives the support 40 in a rapid reciprocatory manner to vibrate the tray 38, distributing the chunks along the width of the tray 38 and moving the chunks in singular fashion therealong to a multi-channel chute 50. The chunks are separated into channels on the multi-channel chute 50 and fed to a multi-channel belt 52 which is conventionally trained around a pair of rollers 54 and 56. A cantilevered support 58 supports the rollers 54 and 56. The multi-channel chute 50 is mounted on a support 49 and is vibrated by a vibratory motor 51 to move the meat chunks down the chute in a controlled manner to the belt 52. The meat chunks 10c are projected at a controlled speed by the belt 52 and through a photometric sensing unit 60.

The photometric sensing unit 60 is formed by an enclosure 61, open at the top and bottom, and a plurality of photocells 62 and 63 mounted at opposite sides thereof in staggered relationship to each other. A plurality of illumination tubes 64 are also mounted within the enclosure 61 to illuminate the meat chunks 10c passing through the photometric sensing unit 60. An air ejector 66, supplied with air through hose 68, is provided beneath the photometric sensing unit 60 and is controlled by control circuits (FIG. 4) to selectively alter the trajectory path of the meat chunks 10c passing through the photometric sensing unit 60. The photocells 62 and 63 are connected to the control circuits to operate the air ejector 66 responsive to a sensed light value of the meat chunks 10c falling through the photometric sensing unit 60. As illustrated in FIG. 3, the ejector 66 is an elongated bar with a plurality of slots 67. One slot is provided for each pair of oppositely disposed photocells 62. Thus, each of the meat chunks 10c fed through the photometric sensing unit 60 will be viewed on opposite sides by a pair of photocells and will pass a slot 67. Each slot 67 is operated by a pair of oppositely disposed photocells aligned therewith. A suitable ejector device which can be used to dispense the air from each of these slots is disclosed and claimed in the patent to Fraenkel U.S. Pat. No. 3,053,497.

Normally, the meat chunks 10c will follow a trajectory path 72 and land on conveyor 70. In the event that the trajectory path is altered by ejector 66, the meat chunks 10c will follow a trajectory path 76 and land on a conveyor 74. A separator plate 75 separates the conveyor belts 70 and 74.

A thermal insulating shroud 78 encloses the vibratory feeder tray 38, the multi-channel chute 50 and the multi-channel belt 52. The shroud 78 is formed by a pair of upstanding side walls 80, a bottom wall 82, and a top wall 81. A glass panel 92 is desirably positioned at the slanted forward portion of the side walls 80 for viewing the meat chunks 10c as they pass along the multi-channel belt 52. The side walls 80, top wall 81 and the bottom wall 82 are made of a thermal insulating material. A forwardly and upwardly extending lip 83 is provided at the front portion of the bottom wall 82 to partially enclose the front portion of the shroud 78, but leaves a sufficient opening to permit passage of the meat chunks 10c.

A table 94 supports the thermal insulating shroud 78 and the feeding equipment therein. Refrigerated air is provided through the upper ducts 86 from a refrigeration heat exchanger 84 in a plenum 90. Air is fed to the plenum 90 by a lower duct 88. The air is drawn through the heat exchanger 84 by a fan 96 mounted in duct 86. Cooling fluid is supplied to the heat exchanger 84 by a conventional refrigeration unit (not shown) housed in cabinet 98.

The refrigerated air supplied to the thermal insulating shroud 78 maintains the meat chunks 10c on the feeding equipment at or near freezing temperature. Desirably, the temperature of the meat chunks 10c and the surface of the vibratory feeder tray 38, the multi-channel chute 50 and the multi-channel belt 52 are maintained at a temperature at or near the freezing temperature which, for meat, is about 26°–32°F. Such a temperature greatly facilitates the handling of the meat chunks so that they can be singularizing and sorted by the photometric sorting unit.

A control circuit for operating one slot of the ejector 66 will now be described with reference to FIG. 4. Each pair of photocells and slot has a similar circuit, but only one such circuit will be described. The output of the photocell 63 is connected to amplifier 100 which amplifies the output signal and applies the amplified signal to a discriminator 102 which is set to produce an output signal when the amplifier output reaches a predetermined level. The discriminator output is alternately coupled to an OR gate 106 or an AND gate 114 through switch 104. Similarly, the output of photocell 62 is amplified in amplifier 108 and applied to discriminator 110. The same level is set on discriminator 110 as on discriminator 102. The discriminator 110 thus turns on when the output signal from the photocell 62 reaches a predetermined level. The output from the discriminator 110 is alternately applied to OR gate 106 or AND gate 114 through switch 112. Switches 104 and 112 are ganged together through means (not shown) so that the output of both discriminators 102 and 110 are simultaneously applied to the OR gate 106 or to the AND gate 114.

The outputs from the AND gate 114 and the OR gate 106 are applied to the ejector 66 through a delay circuit 116 which delays the signal to the ejector 66 sufficiently to permit the meat chunk 10c to fall from the photocells 66, 63 to the ejector 66.

When the discriminator outputs are applied to OR gate 106, the ejector will be activated to eject the meat chunk when the output signal from either photocell 62 or 63 exceeds a predetermined value. Alternatively, when the discriminator outputs are applied to the AND gate 114, the ejector will not be activated to eject the meat chunk unless the output signals from both photocells 62, 63 exceed a predetermined limit.

As an alternate mode of operation, each of the discriminators could be coupled to an inverter and the discriminator set at lower levels so that the ejector would be activated only when the output signals from the photocells fall below a predetermined value. In this alternative mode, the ejectors would be operative to eject meat chunks having a predetermined amount of lean meat.

In operation, the meat chunks 10c are divided into eight different channels by the multi-channel chute 50 and the multi-channel belt 52. The meat chunks 10c are further singularized by the vibratory feeder tray 38 and the multi-channel chute 50. The thus divided and singularized meat chunks 10c are fed seriatim through the photometric sensing unit 60. The light reflected from opposite sides of each meat chunk 10c is detected as it falls through the photometric sensing unit by the photoelectric cells 62 and 63. A signal representative of the light value of each of the opposite sides of the meat chunks 10c is applied to the control circuit (FIG. 4). The amount of fat in any meat chunk 10c is proportional to the light value of the meat chunk. Thus, the higher the reflected light from the meat chunk, the more fat content of the meat chunk. If desired, a green filter can be used in front of the photoelectric cells 62 to accentuate the color or light difference between the lean meat and the fat portions of the meat chunks. With the photocell outputs connected to the OR gate 106, the control circuit is set to operate an ejector 66 for a particular slot 67 when the value of the light detected by either of the aligned corresponding photocells 62 exceeds a predetermined value. When such a value is exceeded, the ejector 66 projects a stream of air after a short delay to deflect the particular detected meat chunk 10c onto a conveyor belt 74. Otherwise, the meat chunks will fall undeflected onto the conveyor belt 70.

With the photocell outputs connected to the AND gate 114, the control circuit is set to operate an ejector 66 for a slot 67 when the value of the light detected by both photocells 62 and 63 exceeds a predetermined value.

The AND gate and OR gate circuits with the switch provides great versatility for the sorting function of the machine. A much higher degree of sensitivity can be achieved with the OR circuit when the fat particles are ejected. Conversely, a higher degree of sensitivity is achieved with the AND circuit when the lean meat particles are ejected.

The detecting and ejection operation takes place separately for each pair of photocells and related air slot 67. For example, a meat chunk in one channel may be ejected while a meat chunk in an adjacent channel passes undeflected onto the conveyor belt 70.

As an alternate system, the control unit can be set to eject all those meat chunks having a light value below a predetermined value. In this alternate system, the meat chunks containing a higher percentage of lean meat would be ejected onto the conveyor belt 74.

The meat chunks are sorted according to their light value or color and consequently chunks of higher lean meat content are sorted from chunks of lower lean meat content. The higher lean meat content chunks can thus be further ground up and used for hamburger or other diverse meat products.

As used herein, "light value" refers to the degree of lightness as seen by a photoelectric cell, for example. "Color" is intended to designate black and white as well as normal spectral colors.

The invention has been described with reference to a system wherein the meat chunks are separated into eight channels or paths. This invention can be practiced with one or more such channels or paths, and the eight-channel system has been described for purposes of illustration.

The invention provides a method and system for upgrading a given quantity of meat products which would be otherwise unsuitable for high grade meat purposes such as hamburger and the like. The kind of meat on which the invention can be used would commonly be suitable for only low quality, high fat products. Such trim meat contains typically about half lean meat and half fat. The invention provides a means and method for upgrading these products to a fraction containing, for example, 75% lean meat and 25% fat which is a saleable meat product for hamburger.

Reasonable variation and modification is possible within the scope of the foregoing disclosure, the drawings and appended claims without departing from the spirit of the invention.

The embodiments of the invention in which an exclusive property or privilege is claimed are defined as follows:

1. A system for processing trim meat pieces having lean meat portions and fat portions, said system comprising:
   means for dividing said trim meat pieces into substantially regular shape meat chunks having higher lean meat content and lower lean meat content;
   means for singularizing said meat chunks;
   means to cool said meat chunks to a low temperature in said singularizing means;
   A photometric sensing means for detecting an optical property related to the lean meat content of said meat chunks;
   means for passing said singularized meat chunks through said photometric sensing means; and
   means to sort said meat chunks according to the value of the optical property thus detected;
   whereby said meat chunks are sorted according to the lean meat content thereof to achieve a fat rich concentrate and a lean meat rich concentrate.

2. A system according to claim 1 wherein said dividing means includes an extruder.

3. A system according to claim 2 wherein said singularizing means includes a vibratory feeder tray and a conveyor belt positioned to receive meat chunks from said vibratory feeder tray, and said conveyor belt projects said meat chunks through said photometric sensing means.

4. A system according to claim 3 wherein said photometric sensing means detects the color of said meat chunks and said sorting means includes means to deflect the trajectory path of said meat chunks according to the color thereof.

5. A system according to claim 4 wherein said photometric sensing means includes means to photometrically sense opposite sides of said meat chunks as said meat chunks pass through said photometric sensing means.

6. A system for sorting substantially regular shape meat chunks having a higher lean meat content from substantially regular shape meat chunks having a higher fat content, said system comprising:
means for singularizing said meat chunks;
a photometric sensing means for detecting an optical property relating to the lean meat content of said meat chunks;
means for passing said singularized meat chunks through said photometric sensing means;
means to sort said meat chunks according to the value of the optical property thus detected; and
means for cooling said meat chunks on said singularizing means and on said passing means to a low temperature to assist in separation and manipulation of said meat chunks;
whereby said meat chunks are sorted according to lean meat content thereof to achieve a fat-rich concentrate and a lean meat rich concentrate.

7. A system for processing trim meat pieces having lean meat portions and fat portions, said system comprising:
means for dividing said trim meat pieces into substantially regular shape meat chunks having higher lean meat content and lower lean meat content;
means for singularizing said meat chunks;
a photometric sensing means for detecting an optical property related to the lean meat content of said meat chunks, said sensing means including means to detect said optical property at opposite sides of said meat chunks;
means for passing said singularized meat chunks through said photometric sensing means; and
means to sort said meat chunks according to the value of the optical property thus detected, said sorting means including means to sort said meat chunks when said optical property at either side of said meat chunks exceeds a predetermined value;
whereby said meat chunks are sorted according to the lean meat content thereof to achieve a fat rich concentrate and a lean meat rich concentrate.

8. A system according to claim 6 wherein said sorting means further includes an AND gate circuit with means to sort said meat chunks only when said optical property detected on both sides thereof exceeds a predetermined value, and switch means for alternately coupling said OR circuit and said AND circuit with said sensing means.

9. A system for processing trim meat pieces having lean meat portions and fat portions, said system comprising:
means for dividing said trim meat pieces into substantially regular shape meat chunks having higher lean meat content and lower lean meat content;
means for singularizing said meat chunks;
a photometric sensing means for detecting an optical property related to the lean meat content of said meat chunks, said sensing means including means to detect said optical property at opposite sides of said meat chunks;
means for passing said singularized meat chunks through said photometric sensing means; and
means to sort said meat chunks according to the value of the optical property thus detected, said sorting means including means to sort said meat chunks only when said optical property detected on both sides thereof exceeds a predetermined value.

* * * * *